United States Patent
Brandão (10) Patent No.: US 11,253,477 B2
(45) Date of Patent: Feb. 22, 2022

(54) COMPOSITIONS BASED ON PROPOLIS NANOCAPSULES WHICH CAN BE USED AS CARRIERS FOR SUBSTANCES OF INTEREST, METHODS FOR PRODUCING SAME AND USE THEREOF

(75) Inventor: Humberto de Mello Brandão, Juiz de Fora (BR)

(73) Assignee: EMPRESA BRASILEIRA DE PESQUISA AGROPECUÁRIA—EMBRAPA, Brasília (BR)

( * ) Notice: Subject to any disclaimer, the term of this patent is extended or adjusted under 35 U.S.C. 154(b) by 0 days.

(21) Appl. No.: 13/882,043

(22) PCT Filed: Oct. 27, 2011

(86) PCT No.: PCT/BR2011/000400
§ 371 (c)(1),
(2), (4) Date: Jul. 19, 2013

(87) PCT Pub. No.: WO2012/054999
PCT Pub. Date: May 3, 2012

(65) Prior Publication Data
US 2013/0295181 A1    Nov. 7, 2013

(30) Foreign Application Priority Data

Oct. 27, 2010 (BR) .............. PI 1004808-1

(51) Int. Cl.
| | |
|---|---|
| A61K 9/14 | (2006.01) |
| A61K 35/644 | (2015.01) |
| A61K 9/51 | (2006.01) |
| A61K 31/7052 | (2006.01) |
| A61K 36/00 | (2006.01) |
| A61K 31/65 | (2006.01) |
| A61K 8/98 | (2006.01) |
| A01N 65/00 | (2009.01) |
| A61K 8/02 | (2006.01) |
| A61Q 19/00 | (2006.01) |
| A01N 25/28 | (2006.01) |
| B82Y 40/00 | (2011.01) |

(52) U.S. Cl.
CPC .............. A61K 9/14 (2013.01); A01N 25/28 (2013.01); A01N 65/00 (2013.01); A61K 8/0241 (2013.01); A61K 8/988 (2013.01); A61K 9/5176 (2013.01); A61K 31/65 (2013.01); A61K 31/7052 (2013.01); A61K 35/644 (2013.01); A61K 36/00 (2013.01); A61Q 19/00 (2013.01); A61K 9/5192 (2013.01); A61K 2800/10 (2013.01); B82Y 40/00 (2013.01); Y10S 977/84 (2013.01)

(58) Field of Classification Search
CPC ......... A61K 9/14; A61K 8/988; A61K 35/644
See application file for complete search history.

(56) References Cited

U.S. PATENT DOCUMENTS

| | | | |
|---|---|---|---|
| 5,133,908 A | 7/1992 | Stainmesse et al. | |
| 2003/0152640 A1* | 8/2003 | Dolak | A61K 35/644 424/539 |
| 2005/0009908 A1* | 1/2005 | Hedberg | A61K 9/5138 514/548 |
| 2008/0214619 A1* | 9/2008 | Wolfe | G06Q 50/22 514/338 |
| 2010/0209535 A1* | 8/2010 | Kiani | A61P 31/12 424/619 |
| 2015/0283286 A1* | 10/2015 | Eastwood | A61K 31/722 424/94.64 |

FOREIGN PATENT DOCUMENTS

| | | | |
|---|---|---|---|
| CN | 1669434 A | * | 9/2005 |
| CN | 1669434 A | * | 9/2005 |

OTHER PUBLICATIONS

Machine translation of CN1669434A created on Jul. 15, 2014.*
EPA "Registration Eligibility Decision for Propylene Glycol and Dipropylene Glycol" Sep. 2006, pp. 1-70.*
Chopra, I.; Roberts, M. "Tetracycline Antibiotics: Mode of Action, Applications, Molecular Biology, and Epidemiology of Bacterial Resistance" Micro Mol Bio Rev 2001, 232-260.*
EPA "Registration Eligibility Decision for Propylene Glycol and Dipropylene Glycol" Sep. 2006, pp. 1-70 (Year: 2006).*
Chopra, I.; Roberts, M. "Tetracycline Antibiotics: Mode of Action, Applications, Molecular Biology, and Epidemiology of Bacterial Resistance" Micro Mol Bio Rev 2001, 232-260. (Year: 2001).*
Bachir, R.G. et al. "Antibacterial activity of the essential oils from the leaves of *Eucalyptus globulus* against *Escherichia coli* and *Staphylococcus aureus*" Asian Pac J Trop Biomed 2012; 2(9): 739-742 (Year: 2012).*

(Continued)

*Primary Examiner* — Andrew S Rosenthal
(74) *Attorney, Agent, or Firm* — Sughrue Mion, PLLC (57) ABSTRACT

A process for obtaining compositions constituted by propolis nanoparticles is disclosed. The nanoparticles are optionally associated to a substance of interest such as active ingredients, and, optionally, substances of secondary effect such as synergists and adjuvants. The process includes preparing a fraction A, which consists of propolis extract dissolved in an organic solvent, to which stabilizer and/or emulsifier may be added, and, optionally, substances of interest and/or of secondary effect; ii) preparing a fraction B, aqueous phase, constituted by: (ii.1) water; or (ii.2) an aqueous solution or dispersion, to which stabilizer and/or emulsifier may be added; (iii) dropping the fraction A onto the fraction B or vice versa; iv) homogenizing the mixture by stirring and spontaneous formation of nanoparticles with average size from 1 to 1000 nm in a dispersion; and v) optionally (v-1) removing organic solvent and/or (v-2) drying the nanodispersion.

24 Claims, 2 Drawing Sheets

(56) References Cited

OTHER PUBLICATIONS

Raghukumar, R. et al. "Antimethicillin-Resistant *Staphylococcus aureus* (MRSA) Activity of 'Pacific Propolis' and Isolated Prenylflavanones" Phytother. Res. 24: 1181-1187 (2010) (Year: 2010).*
McCall, R.L. et al. "PLGA Nanoparticles Formed by Single- or Double-emulsion with Vitamin ETPGS". Vis. Exp. (82), e51015, 2013 (Year: 2013).*
Machine translation of CN1669434A created on Jul. 15, 2014. (Year: 2014).*
Sadlon, A.E. et al. "Immune-Modifying and Antimicrobial Effects of Eucalyptus Oil and Simple Inhalation Devices" Altern Med Rev 2010;15(1):33-47 (Year: 2010).*
International Preliminary Report on Patentability dated Apr. 30, 2013, in International Application No. PCT/BR2011/000400.
Kim, D. et al. Preparation of Propolis Nanofood and Application to Human Cancer, Biological Pharmaceutical Bulletin, V. 31, N. 9, p. 1704-1710, 2008.

* cited by examiner

COMPOSITIONS BASED ON PROPOLIS NANOCAPSULES WHICH CAN BE USED AS CARRIERS FOR SUBSTANCES OF INTEREST, METHODS FOR PRODUCING SAME AND USE THEREOF

This is a National Stage Entry of Application No. PCT/BR2011/000400 filed Oct. 27, 2011, claiming priority based on Brazilian Patent Application No. PI 1004808-1 filed Oct. 27, 2010, the contents of all of which are incorporated herein by reference in their entirety.

FIELD OF THE INVENTION

The present invention relates to a process for obtaining compositions constituted by propolis nanoparticles and to the use thereof, said nanoparticles being optionally associated to one or more substances of interest such as active principles, as well as, optionally, substances of secondary effect such as synergists and adjuvants.

BACKGROUND OF THE INVENTION

Propolis exhibits pharmacological characteristics such as bactericidal characteristics, with action against *Staphylococcus aureus*, Methicillin-resistant *Staphylococcus aureus*, *Escherichia coli*, *Clostridium perfringens*, *Actinomyces israelii*, *Prevotella nigrescens*, *Fusobacterium nucleatum*, *Bacillus subtilis*, among others (FERREIRA, B. A. et al, Antimicrobial effect of propolis and other substances against selected endodontic pathogens, Oral Surgery, Oral Medicine, Oral Pathology, Oral Radiology & Endodontics, v. 16, p. 104-709, 2007); anticarcinogenics (FU, J.; XIA, Y.; ZHENG, Y. Antimutagenicity of propolis against some mutagens in vivo and in vitro, Biomedical and Environmental Sciences, v.17, p. 469-475, 2004); antioxidant (CONEAC, G.; et al. Flavonoid contents of propolis from the west side of Romania and correlation with the antioxidant activity, Chemical Bulletin of "Politechnica", v. 53, n. 67, p. 1-2, 2008); anti-inflammatory (PAULINO, N. et al, Anti-inflammatory effects of a bioavailable compound, Artepillin C, in Brazilian propolis, European Journal of Pharmacology, v. 587, p. 296-301, 2008), as well as high adhesivity to the human skin by virtue of its interaction with oils and tegumentary proteins (BURDOCK, G. A., Review of the biological properties and toxicity of bee propolis (propolis). Food and Chemical Toxicology, v. 36, p. 347-363, 1998).

There is synergism between the components of raw extract of propolis and other compounds, as disclosed in SCHELLER et al. (1999) (SCHELLER, S. et al. Synergism between ethanolic extract of propolis (EEP) and anti-tuberculosis drugs on growth of mycobacteria. Journal of Biosciences, v. 54, n. 7-8, p. 549-53, 1999), FERNANDES JUNIOR (2005) (FERNANDES JUNIOR, A. Propolis: anti-*Staphylococcus aureus* activity and synergism with antimicrobial drugs. Mem Inst Oswaldo Cruz, Rio de Janeiro, v. 100, n. 5, p. 563-566, August 2005) and in CN1864661, or of propolis nanoparaticles associated to plant Ions for disinfection of surfaces, as disclosed in document CN1286373.

Propolis is used in therapeutic and cosmetic formulations, and in products for hygiene, among others. It is commercially available as an extract, tablet or capsule. The latter form of presentation also enables controlled release and is sometimes directed from propolis itself. However, in the known products, it works solely as an active principle.

The production of nanoparticles is an advantageous technology for encapsulating propolis with a view to the controlled release or the release directed from active compositions, or to enable the use of new routs of application of these compositions.

Conventional techniques of producing propolis micro- or nanoparticles, such as those disclosed in documents BR PI0106564-5, US5133908 and CN1406588, aim at only modifying some of its property, such as for example its solubility, as shown in the document by Kim et al in 2008 (KIM, D. et al. Preparation of propolis nanofood and application to human cancer—Biological Pharmaceutical Bulletin, v. 31, no. 9, p. 1704-1710, 2008), and at enabling them to be incorporated into a covering material, either right afterward or concomitantly. When encapsulated into nanoparticles, propolis governs some of the characteristics of the substances that compose the matrix. As an example of this effect we can cite the reduction of the taste of nanoencapsulated propolis, since what comes into direct contact with the taste buds is the polymer that covers the propolis, as cited in document US 20090202635.

However, if propolis is used as a matrix for making nanoparticles (encapsulating agent), propolis itself takes on the characteristics of such particles, thus exhibiting new characteristics. By way of example, azithromycin in its pure form is found in small crystals that have little or no adhesion to the human dermis. Notwithstanding, when azithromycin is nanoencapsulated with propolis, it becomes covered with the latter, which makes the direct contact with the dermis. In this condition and making use of the adhesiveness property of propolis to the human skin (BURDOCK, G. A., Review of the biological properties and toxicity of bee propolis (propolis). Food and Chemical Toxicology, v. 36, p. 347-363, 1998), azitromicyn ends up by adhering to the skin.

Supersonic stirring is one of the techniques used for obtaining propolis nanoparticles, as disclosed in patent documents such as TW200637500, CN1413598, CN1685928. These are homogenization techniques that require high consumption of energy and the use of expensive equipment, more suitable for laboratory use than industrial use. Besides, they may cause alterations in the functionality of active principles by raising the temperature due to the cavitation phenomenon, or else by the degradation of active compounds of the propolis extract by free radicals (ROS—reactive oxygen species), formed during this operation (STANISAVLEJEV et al. Antioxidant and antimicrobial activity of *Echinacea* (*Echinacea purpurea* L.) extracts obtained by classical and ultrasound extraction. Biotechnology and Bioengineering. Chinese Journal of Chemical Engineering, v. 17, n. 3, p. 478-483, 2009).

SUMMARY OF THE INVENTION

The present invention refers to compositions constituted by propolis nanoparticles, optionally associated to one or more substances of interest, such as active principles, as well as, optionally, substances of secondary effect.

The present invention also relates to the process of obtaining compositions constituted by propolis nanoparticles, optionally associated to one or more substances of interest.

The present invention further relates to the uses of compositions constituted by propolis nanoparticles, optionally associated to one of more substances of interest.

The process of obtaining compositions constituted by propolis nanoparticles uses the techniques of: (i) solvent displacement and, optionally, subsequent removal of solvent; or (ii) the technique of forming an emulsion with subsequent removal of the solvent. The emulsion formation technique is used when the solvent is immiscible with water.

The process of obtaining the nanoparticles consists of the following steps:

i) preparing a fraction A, which consists of propolis extract dissolved in an organic solvent in a mass-volume proportion of 0.001 to 40%, to which one may add one or more stabilizers and/or emulsifiers at the concentration of from 0.01 to 20% (m/v), as well as, optionally, add one or more substances of interest and/or of secondary effect;

ii) Preparing a water-phase fraction B constituted by: (ii.1) water; or (ii.2) an aqueous solution or dispersion at the concentration of 0.01 to 20% (m/v), to which one may add one or more stabilizers and/or emulsifiers at the concentration of from 0.0-1 to 20% (m/v);

iii) dropping the fraction A onto the fraction B or the fraction B onto the fraction A;

iv) homogenizing the mixture at a temperature ranging from –2° C. to 90° C. and spontaneous formation of nanoparticles with average size ranging from 1 to 1000 nm in a dispersion, such homogenization taking place under mechanical stirring of 1 (one) to 40000 rpm, when the organic solvent is soluble or partly soluble in water, and 5000 to 25000 rpm when the organic solvent is immiscible with water; or alternatively, the mixture is slowly introduced into a high-pressure piston homogenizer, under mechanical stirring, with the pressure ranging from 0.01 (one hundredth) at 5000 bar, preferably from 1 to 1000 bar, at the temperature of –7 to 140° C. and ambient or modified atmosphere, such as the one composed by an inert gas or a mixture of inert gases;

v) optionally, the following additional steps may be involved: (v-1) removal of the organic solvent; and/or (v-2) drying the nanodispersion and obtaining a powdered product.

The product obtained has particle size that may be modulated by varying the concentrations of the components and of the processing conditions.

Propolis may be used as a material that composes the nanoparticles and may have the function of carrying substances of interest, its biological properties being, for example, added to the final product. Optionally, these properties may be improved since this is a nanostructured system. In addition, propolis is considered a low-cost raw material and is known by the population.

The nanoparticles formed may be used for application in pharmaceutical, agrochemical, cosmetic or chemical composition in general, in combination or not with one of more substances of interest.

DETAILS DESCRIPTION OF THE INVENTION

The object of the present invention are compositions constituted by propolis nanoparticles, optionally associated to one or more substances of interest, such as active principles, as well as, optionally, substances of secondary effect, such as synergistic and adjuvant substances.

For the purpose of the present invention, "substance of interest" is meant as comprising a substance having a therapeutic, cosmetic, protective (protection of materials or living beings against biotic or abiotic agents) antimicrobial or chemical effect, but not limited to this list.

The present invention also relates to the process of obtaining compositions constituted by propolis nanoparticles, optionally associated to one or more substances of interest, such as active principles, as well as, optionally, substances of secondary effects, such as synergistic and adjuvant substances.

The present invention further relates to the uses of compositions constituted by propolis nanoparticles, optionally associated to one of more substances of interest and/or one of more substances of secondary effect.

Additionally, the present invention relates to the use of propolis as a nanocarrier for controlled or directed release of substances of interest and/or substances of secondary effect.

The process of obtaining compositions constituted by propolis nano particles uses the techniques of: (i) displacement of solvent and, optionally, subsequent removal of solvent; or (ii) the emulsion formation technique with subsequent removal of the solvent. The emulsion formation technique is used when the solvent is immiscible with water.

Propolis is a biodegradable material containing, among its constituents, both hydrophobic substances and amphiphilic substances. The latter contribute to making the nanoparticles due to their tendency to self organization. These propolis nanoparticles have properties that may be added to the substances of interest, or still there may be synergism between the components. These consist of one or more hydrophobic or amphiphilic substances or a set of these substances.

None of the documents available in the prior art presents a composition constituted by nanoparticles with the same functionality as those of the present invention, namely: the "substances of interest" include, but are not limited to: proteins, antibiotics, anti-inflammatory substances, hormones, amino acids, antiviral, antifungal, herbicidal, insecticidal, acaricidal, antihelminthic agents, vitamins, minerals, fatty acids, carbohydrates, nitrogenated compounds, antioxidants, anticorrosive agents, photoprotectors, catalysts, lubricants, enzymes, natural extracts (such as essential oils, dyes, syrups and flavoring agents), pigments or dyes.

Substances with secondary effect include, but are not limited to: pharmaceuticals, agrochemical substances, natural extracts, cosmetics or chemicals in general.

Propolis has antimicrobial and antioxidant properties and is considered a low-cost raw material, quite known to the population. In its crude form, propolis is a hard and brittle material with color that ranges from yellow to dark brown, produced by bees with the function of filling cracks and contributing to the asepsis of compartments that need a high degree of hygiene, such as the cells intended for laying eggs. In order to make this material, bees use sprouts, flower buds, barks and resinous exudates of various plants, which cause propolis to have a complex chemical composition, generally containing different concentrations of resins, waxes, essential oils, and an alcohol-soluble fraction or vegetable balm (BURDOCK, G. A. Review of the biological properties and toxicity of bee propolis (propolis), Food and Chemical Toxicology, v. 36, p. 347-363, 1998; PEREIRA, A. s.; SEIXAS, F. R. M. S.: AQUINO NETO F. R. Própolis: 100 anos de persquisa e suas perspectivas futures, Química Nova. V. 25, n. 2, p. 321-326, 2002).

The composition of the extracts depends on the type of solvent used and on the origin of the propolis. Most extracts commercially available are obtained by using alcohols, such as ethanol and methanol. Alcohol extract is composed of vegetable resins, waxes and essential oils, containing phenolic compounds such as polyphenols.

For the purpose of this invention "emulsifier" is a substance that makes it possible to form and maintain a uniform dispersion of two or more immiscible substances. "Stabilizer" is meant to be a substance that makes it possible to maintain a uniform dispersion of two or more immiscible substances.

Nanodimensioning of propolis modifies its physical and chemical characteristics. For example, it may improve its solubility in water or the efficiency of its therapeutic functions, as disclosed in patent document CN1406588. On the other hand, propolis nanoparticles may be associated to other nanoparticles of a material of interest and may govern the characteristics of the particles, as is the case in one of the aspects of the present invention.

"Nanodimensioning" is meant to be the reduction of particle size to values smaller than 1000 nm in at least one of the dimensions (SOPPIMATH, K. S. et al, Biodegradable polymeric nanoparticles as drug delivery devices. Journal of Controlled Release, v. 70, p. 1-20, 2001; REIS et al, Nanoencapsulation I. Methods for preparation of drug-loaded polymeric nanoparticles. Nanomedicine: Nanotechnology, Biology, and Medicine, v. 2, p. 8-21, 2006).

When a body is on nanometric scale, the importance of forces like gravity, friction and inertia decreases while other physical forces began to dominate, as for example the electromagnetic, Van der Waals forces and the Brownian motion. Alteration in the intensity of these forces may impart new properties to the nanoparticle in comparison with the same substance on metric scale, that is to say, this technology may be applied for attributing new properties to the substances or even for increasing their reactivity by nanodimensioning, which may be due to the increase in the surface-volume area ratio. This ratio alteration leads to an increase in the area of contact between the nanoparticles and other substances, thus favoring their interactions and reactions, making them more effective by mass unit.

Modulation of the surface-volume area relation of the original substance also interferes directly with the biologic efficiency, that is to say, it decreases the necessary dose of administered substance for achieving the same effect; one may raise the dose and reduce the risk of toxicity coming from the composition that contains the encapsulated substance or active principle or still increase the effective action of the substance when directioning takes place.

One of the uses of nanoparticles is to carry substances of interest, that is, having the function of nanocarriers for controlled or directed release thereof. In a general way, the materials used for making nanocarriers for controlled or directed release of substances are classified as biodegradable or non-biodegradable. By "biodegradable" one means the material the degradation of which takes place by the action of a biological agent, such as enzyme or microorganism.

The release pattern of the active principle carried by biodegradable nanostructures results in complete degradation and excretion or metabolization of the intermediates in the nanoparticle matrix, and in the case of non-biodegradable nanoparticles, the process of releasing the active principle results from its diffusion from the nanoparticle, and the latter tends to accumulate in the organism or ion the environment. The substances that compose propolis nanoparticles are preferably biodegradable and biotolerable.

The solvent displacement technique is considered a simple and economical option for obtaining colloidal nanodispersions (US5133908, US7348031) and consists in forming an oil-water emulsion between the dispersion of polymer in partly water-soluble solvent containing the substance to be covered and an aqueous phase containing a stabilizer. The subsequent addition of water causes diffusion of the solvent to the external phase, resulting in the formation of nanospheres (QUINTANAR-GUERRERO, D. et al, Preparation and Characterization of Nanocapsules from Preformed Polymers by a New Process Based on Emulsification-Diffusion Technique; Pharmaceutical Research, v. 5, n. 7, July, p. 1056-1062, 1998).

The process according to the present invention generates compositions based on propolis nanoparticles by means of the steps of:

i) preparing a fraction A, which consists of propolis extract dissolved in an organic solvent in a mass-volume proportion of 0.001 to 40%, preferably of 0.1 to 20%, that allows the formation of nanoparticles, to which one may add one or more stabilizers and/or emulsifiers at the concentration of from 0.01 to 20% (m/v), preferably of 0.1 to 5%, as well as, optionally, add one or more substances of interest and/or of secondary effect;

ii) preparing a water-phase fraction B constituted by: (ii.1) water; or (ii.2) an aqueous solution or dispersion at the concentration of 0.01 to 20% (m/v), to which one may add one or more stabilizers and/or emulsifiers at the concentration of from 0.01 to 20% (m/v);

iii) dropping the fraction A onto the fraction B or the fraction B onto the fraction A;

iv) homogenizing the mixture at a temperature ranging from −2° C. to 90° C. and spontaneous formation of nanoparticles with average size ranging from 1 to 1000 nm in a dispersion, such homogenization taking place by mechanical stirring with 1 (one) to 40000 rpm, when the organic solvent is soluble or partially soluble in water, and 5000 to 25000 rpm when the organic solvent is immiscible with water; or alternatively, the mixture is slowly introduced into a high-pressure piston homogenizer under mechanical stirring, with the pressure ranging from 0.01 (one hundredth) at 5000 bar, preferably from 1 to 1000 bar, at the temperature of −7 to 140° C. and ambient or modified atmosphere, such as the one composed by an inert gas or a mixture of inert gases;

v) optionally, the following additional steps may be involved: (v-1) removing the organic solvent; and/or (v-2) drying the nanodispersion and obtaining a powdered product.

The product obtained has particle size that can be modulated by varying the concentrations of the components and the operation conditions.

The aqueous phase that composes the fraction B is composed exclusively by water or an aqueous solution or dispersion comprising one or more substances, although without limitation to these, selected from the following group: biodegradable or non-biodegradable and biocompatible or non-biocompatible polymer selected from the group consisting of acrylic acid polymers, alginates, biosynthetic gums, starches, modified starches, cellulose esters, cellulose compounds, gelatins, hydrocolloids, hyaluronic acid, glycols, natural gums, polyacrylates, polyethylene oxides, vinyl-derived polymers, acacia gum, agar gum, gum Arabic, carboxymethylcellulose, carboxyvinyl, carrhageen, casein, cellulose acetate, chitosane, chitin, collagen, dextran, dextrin, cyclodextrins, levan, ethylcellulose, albumin, hydroxyethylcellulose, hydroxyethylmethylcellulose, hydroxypropylmethylcellulose, hydroxypropylcellulose, homopolysaccharides, heteropolysaccharides, polyethyleneglycol and its copolymers, pectin, polyethylenes and irs copolymers, polyvinyl alcohols, polyvinylpyrrolidone, xantan, zeins, polycaprolactone and its polymers, lactic polyacid and its copolymers, glycolic polyacid and its copolymers, polyhydroxybutyrate and its copolymers, polydroxyvalerate and its copolymers, polymethylmetacrylate and its copolymers, polyethylcyanoacrylate and its copolymers, polybutylcyanoacrylate and its copolymers, polyhexylcyanoacrylate and its copolymers, polyisohexylcyanatoacrylate and its copolymers, polyacrylamides, polyurethanes and its copolymers, polystyrene and its copolymers, polyvinylpyridins and their copolymers pyridine and their copolymers, polyacroleines and their copolymers, polyamides, polyphenyl esters and polyurethanes, either isolated or in combination at different proportions.

The solvent used is selected from the group consisting of ethanol, isopropanol, n-butanol, sec-butyl alcohol, ter-butyl alcohol, ethyl ether, diethyl ether petroleum ether, methyl ether, dimethyl ether, benzyl alcohol, propyleneglycol, polypropyleneglycol, dimethylsulfoxide, ethyleneglycol, n-propyl alcohol, methyl alcohol, acetone, propanone, butanone, butanodione, dichloromethane, trichloromethane, polyethyleneglycol, glacial acetic acid, carbon tetrachloride, perchlorethylene, methylene chloride, n-hexane, styrene, xylene, toluene, benzene, ethyl acetate, 1,4-dioxane, tetrahydrofurane (THF), acetonitryl, dimethylformamide, n-butanol, n-propanol, formic acid, cyclohexane, or aqueous solutions of such solvents or mixtures thereof. Preferably, ethanol, acetone, dichloromethane, trichloromethane or hexane is used.

The stabilizer or emulsifier or combination of sterilizers or emulsifiers, if added to the aqueous phase or to the organic phase, is used at a concentration ranging from 0.01 to 20% (m/v), preferably from 0.1 to 5% (m/v), and is selected from the group consisting of, but not limited to alginic acid, polyvinyl alcohols, alginates, agar agar, carrhageen, cellulose and its derivatives, cetyldimeticones, copolyols, detergents, dodecyl sodium sulfate, lecithin, sucrose fatty esters, esters of fatty acids with polyglycerol, esters of castor oil acid interesterified with polyglycerol, esters of fatty acids with propyleneglycol, phospholipids, gums, starched pectin, polyethyleneglycol and its copolymers, polyethylenes and their copolymers, polyoxyethylenes and their copolymers, ethylene oxide, polysorbate and its derivatives, polyvinylpyrrolidone, amphiphilic proteins, mono- and di-glycerides, soaps, glycerol monoestearate, sodium oletate, ammonia phosphate, sucrose acetate isobutyrate, homopolysaccharides, heteropolysaccharides, esteraroyl-2-lactyl sodium lactate, sodium citrate, disodium phosphate, estearylamine, oleylamine, 1-2-dioleoyl-3-trimethyl-ammonium propane, alkylsulfates, 2-dodecoxyethanol, Carbopol®, polyoxyethylene lauryl ether and SPAN®. Preferably, polyvinyl alcohol, phospholipids or polysorbates are used.

The homogenization takes place by mechanical stirring, simultaneously with dropping and at a temperature of from −2° C. to 90° C. Alternatively, the mixture is introduced slowly in a high-pressure piston homogenizer, under mechanical stirring, the pressure ranging from 0.01 (one hundredth) to 5000 bar, preferably from 1 to 1000 bar, at a temperature ranging from −7 to 140° C. and in ambient or modified atmosphere, as composed by an inert gas or a mixture of inert gases. The nanoparticles thus formed have an average diameter ranging from 1 to 1000 nm in dispersion. The homogenization step always involves a physical treatment of the mixture, the main selected option for this invention being the technique based on mechanical stirring, either involving a simple agitator or with a homogenizer under high pressure, as it preserves the active ingredient(s) and other substances that compose the system. As a result, the homogenization technique based in ultrasound is not considered herein to be ideal, although it is a feasible alternative, therefore being viewed as one of the secondary embodiments of the present invention.

The removal of the organic solvent takes place by centrifugation, followed or not by drying of the nanoparticles, simple evaporation, rotationevaporation, lyophilization, spray drying, liquid-liquid extraction or carbonization of the organic solvent with acids.

One aspect of the invention refers to a propolis nanoparticle composition consisting of propolis, organic solvent, water, optionally stabilizers and/or emulsifiers, optionally one or more substances of interest, as well as, optionally, one or more substances of secondary effect, composing a dispersion constituted by nonoparticles with particle size ranging from 1 to 1000 nm of propolis associated to said compounds in a liquid medium.

Another aspect of the invention refers to a propolis nanoparticle composition consisting of propolis, water, optionally stabilizers and/or emulsifiers, optionally one or more substances of interest, as well as, optionally one of more substances of secondary effect, composing a dispersion constituted by nanoparticles with size ranging from 1 to 1000 nm of propolis associated to said components in a liquid medium.

A further aspect of the invention refers to a propolis nanoparticle composition consisting of propolis, water, optionally stabilizers and/or emulsifiers, optionally one or more substances of interest, as well as, optionally, one or more substances of secondary effect, composing a powder product constituted by nanoparticles with size ranging from 1 to 1000 nm of propolis associated to at least one said component.

In another aspect of the invention, propolis is used as a material that composes the nanoparticles, its properties being added to the substance or substances of interest to which they are associated, there being a synergistic effect between the propolis nanoparticles and the substance or substances of interest, and these known properties of propolis can still be potentiated, since this is a nanostructured system. Such substances of interest consist of pharmaceuticals, agrochemicals, cosmetics or chemicals in general.

In another aspect of the invention, the properties of propolis are added to the substance of interest, there being an additive effect between the carrier material and the active ingredient or the combination of active principles, and these known biological properties of propolis can still be potentiated, since this is a nanostructured system. Additionally, when acting as a carrier material, the propolis nanoparticles can promote sustained release or even direct the substance of interest. Such substances of interest consist of pharmaceuticals, agrochemicals, cosmetics or chemicals in general.

Belonging to the family Myrtaceae, *Eucalyptus* globules, *Eucalyptus citriodora* and *Eucalyptus straigeriana* are species whose essential oil obtained from their leaves has a known pharmaceutical use as anti-inflammatory, analgesic, antioxidant, antimicrobial, insecticidal and larvicidal agent (MACEDO, I. T. F. et al. Atividade ovicida e larvicida in vitro do oleo essencial de *Eucalyptus* globules sobre *Haemonchus contortus*. Ver. Bras. Parasitol. Vet., Jacobicabal, v. 18, n. 3, p. 68-66, jul-set. 2009). Among the components of the essential oil, monoterpenes, secondary metabolytes such as 1,8-cineol or eucalyptol, are potentially toxic to insects and most of them non-toxic to mammalians (CHAGAS, A. C. S., et al. Efeito acaricida de oleos essenciais e concentrados emulsionaveis de *Eucalyptus* spp em *Boophilus microplus*. Braz. J. vet. Res. Aniom. Sci., Sao Paulo, v. 39, n. 5, P. 247-253, 2002).

Macrolides are a group of antibiotics that inhibit the synthesis of protein by bacterium in the ribosomes 50S, characterized by containing, in their structure, a macrocyclic ring and a lactone. Among the macrolides are azthromycin, clarithromycin, roxythromycin and erythromycin.

Tetracyclines such as tetracycline, minocycline and doxixycline are antimicrobial compounds considered to have a bacteriostatic effect and applied for human or veterinary use. Since tetracycline has, in its structure, groups capable of forming intramolecular hydrogen bonds, it has chelating properties and forms soluble complexes with metallic iron, calcium, magnesium and aluminum ions in neutral pH. In the form of hydrochlorides, tetracyclines are soluble in water. These molecules bind irreversibly to the ribosom 30S and inhibit binding of aminoacyl-t-RNA to the receptor site in the ribosome 70S.

Example 1

Encapsulation of *Eucalyptus* Essential Oil in Propolis Extract and its Larvicidal Effect on *Amblyomma cajennense*

Figure 1:
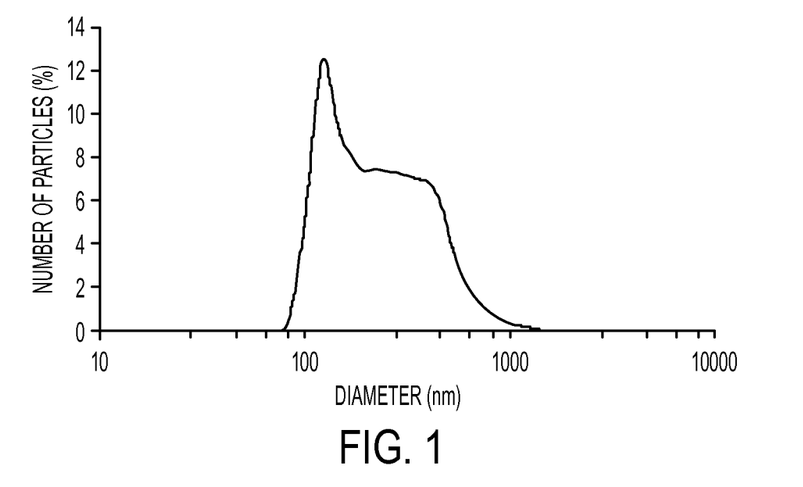
FIG. 1—distribution of particle size (diameter) in nanometers, as a function of the number of propolis nanoparticles containing *Eucalyptus* globules oil.

An alcoholic propolis extract at 2.75% of dry matter was obtained by diluting an original extract containing 13.75% of dry matter. 0.275 mg *Eucalyptus* globules essential oil was added to the extract. 1 mL of the mixture of propolis extract and essential oil was slowly dropped on 5 mL of an aqueous polyvinyl alcohol (PVA) at 0.3%, which was under constant stirring at 600 rpm and kept at 35° C. An emulsion formed spontaneously. The alcoholic extract and the aqueous emulsion were previously filtered through 0.22 mlcrometer nylon filters. The size distribution was determined by dynamic light spreading as shown in FIG. 1. The average diameter of the particles obtained was of 438.1 nm, Zeta potential of −31.5 mV and polydispersion rate of 0.267. An encapsulation efficiency (EE) of 73% was determined by gas chromatography analysis.

In vivo tests were carried out to determine the larvicidal efficacy of the oil encapsulated in propolis nanoparticles against larvae of *Amblyomma cajennense*. Oil/water emulsions were produced, which contained, respectively, 2.5, 5 and 10% of *Eucalyptus* globules oil. The emulsions were compared with propolis nanoparticle suspensions containing encapsulated *Eucalyptus* globules oil, the oil contents being of 1.42, 2.5, 5 and 10% based on the final suspension volume.

TABLE 1

Larvicidal efficiency (*Amblyomma cajennense*) of *Eucalyptus* globules oil encapsulated in propolis nanoparticles or mixed with water.

| Sample | Concentration of *Eucalyptus* globules essential oil in the propolis nanoparticles emulsion or suspension (%) | Larvicidal efficiency (%) |
|---|---|---|
| Non-encapsulated oil | 2.5 | 90 |
| Non-encapsulated oil | 5 | 100 |
| Non-encapsulated oil | 10 | 100 |
| Oil in propolis nanoparticles | 1.42 | 100 |
| Oil in propolis nanoparticles | 2.5 | 100 |
| Oil in propolis nanoparticles | 5 | 100 |
| Oil in propolis nanoparticles | 10 | 100 |

As shown in Table 1, the efficiency of the larvicidal activity of *Eucalyptus* globules in the tested conditions began to decrease in contents of oil lower than 5%, that is, this was the minimum content in which the oil exhibited activity. In order to consider a product as being of high efficiency, the latter must be of at least 95%, which was not the case for the non-encapsulated form. In the nanoencapsulated material, at concentrations as low as 1.42% of oil in the final volume, the efficiency of 100% was maintained, thus improving the effect of the essential oil.

Example 2

Obtention of Propolis Nanoparticles and their Bactericidal Effect

An alcoholic propolis extract at 2.75% and at 0.5% ofn dry matter was obtained by diluting original extract containing 13.75% of dry matter. 1 mL of one of the propolis extracts was slowly dropped in 5 mL of an aqueous solution of polyvinyl alcohol (PVA) at 0.3%, which was under constant stirring at 600 rpm and kept at 35° C. In both cases, an emulsion formed spontaneously. The propolis extract and the aqueous solution had been previously filtered through 0.22-micrometer nylon filters.

Figure 2:
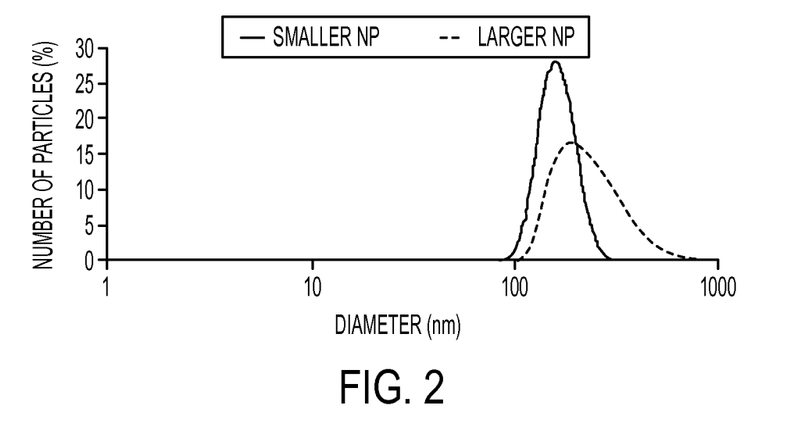
FIG. 2—distribution of particle size (diameter) ion nanometers, as a function of the number of propolis nanoparticles; larger NP (nanoparticies) are particles with an average diameter of 380.4 nm; smaller NP (nanoparicles) are particles with an average diameter of 250.0 nm.

The size distribution was determined by dynamic spread of light as observed in FIG. 2. The particles obtained were divided into two groups; those of an average diameter of 380.4 nm, which exhibited Zeta potential=−38.3 mV and a polydispersion index of 0.065; and those having an average diameter of 250 nm, with Zeta potential of −22.9 mV and polydispersion index of 0.197.

The propolis nanoparticles concentrations in the two formulations wee adjusted to 2048 µg/mL and the bactericidal effect was determined in vitro against samples of *Staphylococcus aureus* (strain ATCC23273) cultivated in Mueller Hinton culture broth.

According to Table 2, which shows the results of the bactericidal efficiency of the nanoparticles, the reduction in the nanoparticle size and the consequent increase in their surface area as a function of the mass were responsible for the greater inhibitory activity of propolis in smaller particles. This could be confirmed by the inhibition of the bacterial growth. Nanoparticles with an average diameter of 380.4 nm needed a minimum concentration of 512 µg/mL of propolis, while the smaller nanoparticles (with 250 nm) needed only 256 µg/mL.

TABLE 2 bactericidal efficiency (*Staphylococcus aureus*, strain ATCC23273) of aqueous suspension of propolis nanoparticles with average diameter of 380.4 nm and 250 nm.

| Dilution factor (μg/mL) | Growth of *Staphylococcus aureus* | |
| --- | --- | --- |
| | NP 380.4 nm | NP 250 nm |
| 32 | + | + |
| 64 | + | + |
| 128 | + | + |
| 256 | + | − |
| 512 | − | − |
| 1024 | − | − |
| 2048 | − | − |

NP 380 nm: nanoparticles with average diameter of 380 nm
NP 250 nm: nanoparticles with average diameter of 250 nm

Example 3

Encapsulation of Tetracycline in Propolis Extract

An alcoholic propolis extract at 2.75% of dry matter was obtained by dilution of original extract containing 13.75% of dry matter. 1 mg/mL of tetracycline was added to the extract. 1 mL of the mixture of propolis extract and tetracycline was slowly dropped into 5 mL of an aqueous solution of polyvinyl alcohol (PVA) at 0.3%, which was under constant stirring at 600 rpm and kept at 35° C. An emulsion was formed spontaneously. The alcoholic extract and the aqueous solution had been previously filtered through 0.22-micrometer nylon filters. The size distribution was determined by dynamic spread of light and the encapsulation efficiency (E.E.) by analysis of visibleultraviolet absorption spectrometry.

The average diameter of the obtained particles was of 371 nm, the Zeta potential was of −18.6 mV and the polydispersion index was 0.335. The encapsulation efficiency (E.E.) was of 26%.

Figure 3:
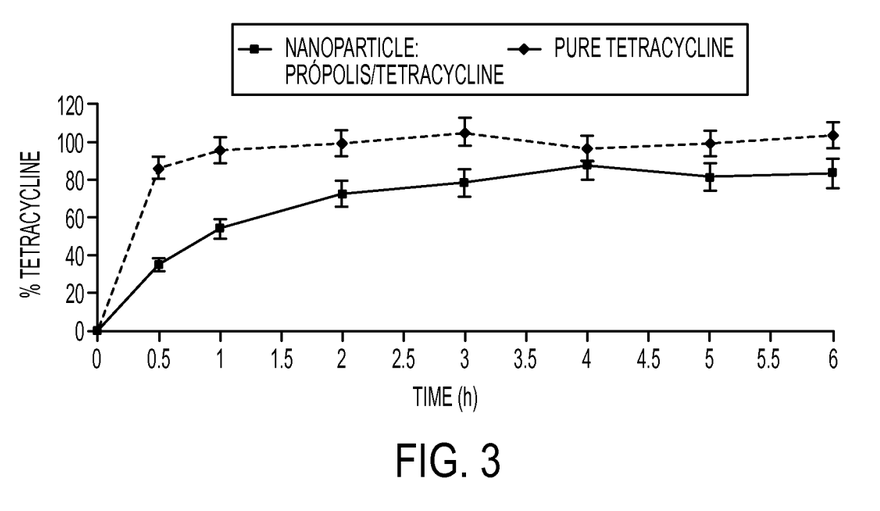
FIG. 3—curve of encapsulated and non-encapsulated tetracycline release.

The release pattern was determined at the temperature of 37° C., with the aid of dialysis membranes in a PBS medium, pH 7.2, plus 10% alcohol, observing the Sink condition. In the first hour there was release of 54% of the encapsulated antibiotic. In the sixth hour of test release of 83% of the encapsulated antibiotic was observed, as shown in FIG. 3.

Example 4

Encapsulation of Azithromycin in Propolis Extract and the Bactericidal Effect Thereof An alcoholic propolis extract at 2.75% of dry matter was obtained by dilution of original extract containing 13.75% of dry matter. 0.83 mL of azithromycin was added to the extract. 1 mL of the mixture of propolis extract and tetracycline was slowly dropped into 5 mL of an aqueous solution of polyvinyl alcohol (PVA) at 0.3%, which was under constant stirring at 600 rpm and kept at 35° C. An emulsion was formed spontaneously. The alcoholic extract and the aqueous solution had been previously filtered in 0.22-micrometer nylon filters. The size distribution was determined by dynamic spread of light. The average diameter of the obtained particles was of 322 nm, Zeta potential of −15.1 mV and polydispersion index of 0.26. The encapsulation efficiency (E.E.) of 57% was determined by analysis of visibleultraviolet absorption spectrometry.

The bactericidal/bacteriostatic effect of the propolis nanoparticles, of nanoencapsulated arithromycin in propolis extract and of pure arithromycin was determined in vitro against samples of Staphylocossus aureus (strain ATCC23273) cultivated in Mueller Hinton culture broth, according to Table 3. Since azithromycyn is a bacteriostatic antibiotic, the samples of the different dilutions were used to determine the core of colony forming units (UFC) in agar BHI (brain-heart-infusion), and thereby determine the bactericidal/bacteriostatic effect shown in Table 4.

TABLE 3

Bactericidal/bacteriostatic efficiency (*Staphylocossus aureus*, strain ATCC23273) of arithromycin (A), of arithromycin nanoencapsulated in propolis extract (AP) and of pure propolis nanoparticles (NP) in Mueller Hinton culture broth.

| | Concentration of azithromycin μg/mL | | | | | | | |
| --- | --- | --- | --- | --- | --- | --- | --- | --- |
| | 512 | 256 | 128 | 64 | 32 | 16 | 8 | 4 |
| A | − | − | − | − | − | − | + | + |
| AP* | − | − | − | − | − | − | + | + |
| NP | − | − | + | + | + | + | + | + |

A = azithromycin;
AP = azithromycin nanoencapsulated in propolis;
NP = propolis nanoparticles
*The value was calculated as a function of the concentration of nanoencapsulated azithromycin.

TABLE 4

Colony forming unites (CFU) in agar BHI of samples of *Staphyloccocus aureus*, strain ATCC23273, from a test of bactericidal/bacteriostatic efficiency of azithromycin (A), of azithromycin nanoencapsulated in propolis extract (AP) and of pure propolis nanoparaticles (NP) in Mueller Hinton culture broth.

| | UFC | | | | | | | |
| --- | --- | --- | --- | --- | --- | --- | --- | --- |
| Origin tube | 512 | 526 | 128 | 64 | 32 | 16 | 8 | 4 |
| A | 0 | 0 | 0 | 1 | 1 | 3 | 30 | i |
| AP* | 0 | 0 | 0 | 0 | 0 | 0 | 28 | i |
| NP | 0 | 0 | i | i | i | i | i | i |

A = azithromycin;
AP = azithromycin nanoencapsulated in propolis;
NP = propolis nanoparticle
*The value was calculated as a function of the concentration of nanoencapsulated azithromycin.
i = uncountable Azthromycin is widely known as a bacteriostatic antibiotic and, in determined concentrations, bactericidal antibiotic. In the tests carried out, when used in the pure form and in concentrations equal to or higher than 128 μg/mL, this antibiotic had a bactericidal effect on *Staphylococcus aureus*. Among the concentrations of 8 and 64 μg/mL azithromycin exhibited a bacteriostatic effect. On the other hand, pure propolis nanoparticles, in concentrations equal to or higher than 256 μg/mL, exhibited exclusively bactericidal activity. In turn, when azithromycin was nanoencapsulated in propolis extract, one achieved a bactericidal effect in quite lower concentrations, for example, of 16 μg/mL, and bacteriostatic in the concentration of 8 μg/mL. Such results prove the synergistic effect of the process of encapsulating azithromycin with propolis nanoparticles.

Example 5

Obtention of Propolis Nanoparticles

A propolis extract in trichloromethane (chloroform) at 0.16% of dry matter was prepared. 1 mL of one of the propolis extracts was slowly dropped into 60 mL of a polyvinyl alcohol (PVA) aqueous solution at 0.3%, which was under constant stirring at 25000 rpm with the aid of a turrax-type homogenizer and kept at 35° C. After formation of an emulsion, the latter was kept under stirring at a rotation of 600 rpm at room temperature until complete evaporation of the chloroform. Both the propolis extract and the aqueous solution had been previously filtered in 0.22-micrometer nylon filters.

Figure 4:
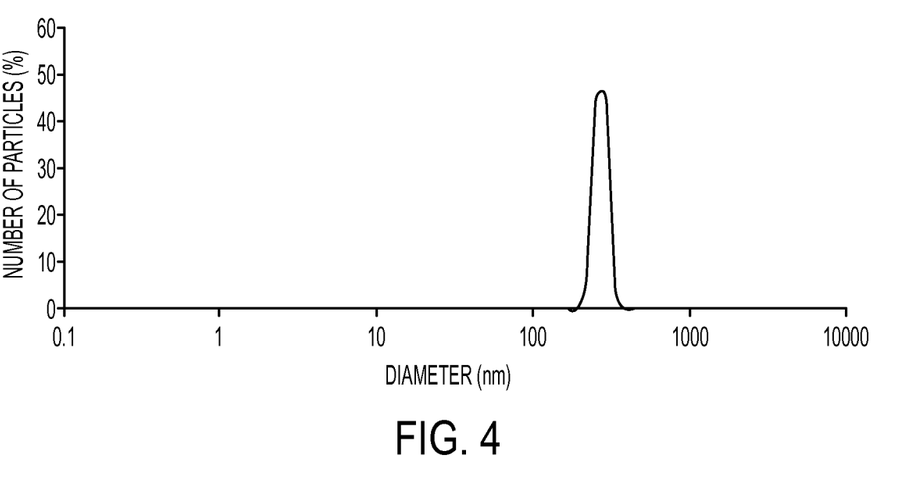
FIG. 4—distribution of particle size (diameter) in nanometers, as a function of the number of propolis nanoparticles.

By dynamic spread of light one observed that particles with average diameter ranging from 220.2 nm to 342 nm (FIG. 4) were formed, with Zeta potential of −1.34 nV.

Example 6

Obtention of Propolis Nanoparticles

A propolis extract in trichloromethane (chloroform) at 0.16% of dry matter was prepared. 100 mL of one of the propolis extracts was mixed to 2000 mL of a polyvinyl alcohol (PVA) aqueous solution at 0.3%. The mixture, under mechanical stirring, was then slowly introduced into a high-pressure piston homogenizer at room temperature and atmosphere and work pressure of 250 bar. After formation of an emulsion, the latter was kept under stirring at 600 rpm at room temperature until complete evaporation of the chloroform. Both the propolis extract and the aqueous solution had been previously filtered in 0.22-micrometer nylon filters. The experiment was carried out in quadruplicate.

By dynamic spread of light, one observed that particles with average diameter ranging from 289.8 nm to 353 nm were formed.

The invention claimed is:

1. A propolis nanoparticles composition consisting of propolis nanoparticles, organic solvent, water, a *Eucalyptus* essential oil, optionally one or more stabilizers and/or emulsifiers, optionally one or more substances of interest, and optionally one or more substances of secondary effect,
   wherein the *Eucalyptus* essential oil is encapsulated in the propolis nanoparticles in the form of a core-shell structure where the propolis is the shell and the *Eucalyptus* oil is in the core,
   wherein the propolis nanoparticles have a size ranging from 1 to 1000 nm, and
   wherein the propolis nanoparticles are obtained by the steps of:
   i) preparing a fraction A, which consists of propolis extract dissolved in the organic solvent at a mass-volume proportion ranging from 0.001 to 40%, to which the *Eucalyptus* essential oil is added, as well as optionally the one or more stabilizers and/or emulsifiers at a concentration ranging from 0.01 to 20% (m/v), optionally the one or more substances of interest, and optionally the one or more substances of secondary effect;
   ii) preparing a fraction B, in aqueous phase, comprising: (ii.1) water; or (ii.2) an aqueous solution or dispersion at a concentration ranging from 0.01 to 20% (m/v), to which the one or more stabilizers and/or emulsifiers may be added at a concentration ranging from 0.01 to 20% (m/v);
   iii) dropping the fraction A onto the fraction B or the fraction B onto the fraction A; and
   iv) homogenizing the mixture and spontaneous forming the propolis nanoparticles with average size ranging from 1 to 1000 nm in a dispersion, such homogenization taking place by mechanical stirring,
   wherein the one or more substances of secondary effect is one or more selected from the group consisting of an adjuvant, a pharmaceutical, an agrochemical, and a cosmetic, and
   wherein the one or more substances of interest is one or more selected from the group consisting of an antioxidant, an anticorrosive agent, a photoprotector, a catalyst, a lubricant, a dye, a tetracycline, and an azithromycin.

2. The propolis nanoparticles composition according to claim 1, wherein the propolis nanoparticles are obtained by the steps of:
   i) preparing a fraction A, which consists of propolis extract dissolved in the organic solvent at a mass-volume proportion ranging from 0.001 to 40%, to which the *Eucalyptus* essential oil is added, as well as optionally the one or more stabilizers and/or emulsifiers at a concentration ranging from 0.01 to 20% (m/v), optionally the one or more substances of interest, and optionally the one more substances of secondary effect;
   ii) preparing a fraction B, in aqueous phase, comprising: (ii.1) water; or (ii.2) an aqueous solution or dispersion at a concentration ranging from 0.01 to 20% (m/v), to which the one or more stabilizers and/or emulsifiers may be added at a concentration ranging from 0.01 to 20% (m/v);
   iii) dropping the fraction A onto the fraction B or the fraction B onto the fraction A; and
   iv) homogenizing the mixture at a temperature ranging from −2° C. to 90° C. and spontaneous forming the propolis nanoparaticles with average size ranging from 1 to 1000 nm in a dispersion, such homogenization taking place by mechanical stirring at 1 (one) to 40000 rpm, when the organic solvent is soluble or partially soluble in water, and at 5000 to 25000 rpm when the organic solvent is immiscible in water.

3. The propolis nanoparticles composition according to claim 1, wherein the propolis nanoparticles are obtained by the steps of:
   i) preparing a fraction A, which consists of propolis extract dissolved in an organic solvent at a mass-volume proportion ranging from 0.001 to 40%, to which the *Eucalyptus* essential oil is added, along with optionally the one or more stabilizers and/or emulsifiers at a concentration ranging from 0.01 to 20% (m/v), and optionally the one or more substances of interest and/or of secondary effect;
   ii) preparing a fraction B, in aqueous phase, comprising: (ii.1) water; or (ii.2) an aqueous solution or dispersion at a concentration ranging from 0.01 to 20% (m/v), to which the one or more stabilizers and/or emulsifiers may be added at a concentration ranging from 0.01 to 20% (m/v);
   iii) dropping the fraction A onto the fraction B or the fraction B onto the fraction A; and
   iv) under mechanical stirring, slowly introducing the mixture of A with B into a high-pressure piston homogenizer with the pressure ranging from 0.01 (one hundredth) under 5000 bar at a temperature ranging from -7 to 140° C. and at ambient or modified atmosphere, such as composed by an inert gas or a mixture of inert gases.

4. The propolis nanoparticles composition according to claim 1, characterized in that said mass-volume proportion of propolis extract dissolved in an organic solvent ranges from 0.1 to 20%.

5. The propolis nanoparticles composition according to claim 1, characterized in that said aqueous phase is composed of the aqueous solution or dispersion, and the aqueous solution or dispersion contains one or more substances selected from the group consisting of acrylic acid polymers, alginates, biosynthetic gums, starches, modified starches, cellulose esters, cellulose compounds, gelatins, hydrocolloids, hyaluronic acid, glycols, natural gums, polyacrylates, polyethylene oxides, vinyl-derived polymers, acacia gum, agar gum, gum Arabic, carboxymethylcellulose, carboxyvinyl, carrageen, casein, cellulose acetate, chitosan, chitin, collagen, dextran, dextrin, cyclodextrins, levan, ethylcellulose, albumin, hydroxyethylcellulose, hydroxyethylmethylcellulose, hydroxypropylmethylcellulose, hydroxypropylcellulose, homopolysaccharides, heteropolysaccharides, polyethyleneglycol and its copolymers, pectin, polyethylene and its copolymers, polyvinyl alcohols, polyvinylpyrrolidone, xanthan, zeins, polycaprolactone and its polymers, lactic polyacid and its copolymers, glycolic polyacid and its copolymers, polyhydroxybutyrate and its copolymers, polydroxyvalerate and its copolymers, polymethylmetacrylate and its copolymers, polyethylcyanoacrylate and its copolymers, polybutylcyanoacrylate and its copolymers, polyhexylcyanoacrylate and its copolymers, polyisohexylcyanatoacrylate and its copolymers, polyacrylamides, polyurethanes and its copolymers, polystyrene and its copolymers, polyvinylpyridines and their copolymers, pyridine and its copolymers, polyacroleins and their copolymers, polyamides, polyphenyl esters, and polyurethanes.

6. The propolis nanoparticles composition according to claim 1, characterized in that one or more stabilizers and/or emulsifiers employed in steps (i) and/or (ii) optionally are present at a concentration ranging from 0.1 to 5% (m/v).

7. The propolis nanoparticles composition according to claim 1, characterized in that the one or more stabilizers and/or emulsifiers in the organic phase and the aqueous phase are independently selected from the group consisting of alginic acid, polyvinyl alcohols, alginates, agar, carrageen, a cellulose, cetyldimeticones, copolyols, detergents, dodecyl sodium sulfate, lecithin, sucrose fatty esters, esters of fatty acids with polyglycerol, esters of castor oil acid interesterified with polyglycerol, esters of fatty acids with propyleneglycol, phospholipids, gums, starched pectin, polyethyleneglycol and its copolymers, polyethylenes and their copolymers, polyoxyethylenes and their copolymers, ethylene oxide, a polysorbate, polyvinylpyrrolidone, amphiphilic proteins, mono- and di-glycerides, soaps, glycerol monostearate, sodium oleate, ammonia phosphate, sucrose acetate isobutyrate, homopolysaccharides, heteropolysaccharides, esteraroyl-2-lactyl sodium lactate, sodium citrate, disodium phosphate, stearylamine, oleylamine, 1-2-dioleoyl-3-trimethyl-ammonium propane, alkylsulfates, 2-dodecoxyethanol, and polyoxyethylene lauryl ether.

8. The propolis nanoparticles composition according to claim 1, characterized in that said stabilizer and/or emulsifier consists of polyvinyl alcohol, phospholipids and/or polysorbates.

9. The propolis nanoparticles composition according to claim 1, characterized in that the organic phase (i) and the aqueous phase (ii) exhibit a concentration of one or more emulsifiers and/or stabilizers at a concentration ranging from 0.1 to 5% (m/v).

10. The propolis nanoparticles composition according to claim 1, characterized in that the one or more substances of interest is selected from the group consisting of a tetracycline and an azithromycin.

11. The propolis nanoparticles composition according to claim 1, characterized in that the one or more substances of secondary effect consist of an adjuvant.

12. The propolis nanoparticles composition according to claim 1, characterized in that said organic solvent consists of one or more selected from the group consisting of ethanol, isopropanol, n-butanol, sec-butyl alcohol, tert-butyl alcohol, ethyl ether, diethyl ether petroleum ether, methyl ether, dimethyl ether, benzyl alcohol, propyleneglycol, polypropyleneglycol, dimethylsulfoxide, ethyleneglycol, n-propyl alcohol, methyl alcohol, acetone, propanone, butanone, butanodione, dichloromethane, trichloromethane, polyethyleneglycol, glacial acetic acid, carbon tetrachloride, perchlorethylene, methylene chloride, n-hexane, styrene, xylene, toluene, benzene, ethyl acetate, 1,4-dioxane, tetrahydrofurane (THF), acetonitrile, dimethylformamide, n-butanol, n-propanol, formic acid, and cyclohexane.

13. The propolis nanoparticles composition according to claim 1, characterized in that said organic solvent is one or more selected from the group consisting of ethanol, acetone, dichloromethane, trichloromethane and hexane.

14. A propolis nanoparticle composition in the form of a dispersion consisting of propolis nanoparticles, organic solvent, water, a *Eucalyptus* essential oil, optionally one or more stabilizers and/or emulsifiers, optionally one or more substances of interest, and optionally one or more substances of secondary effect, wherein the *Eucalyptus* essential oil is encapsulated in the propolis nanoparticles in the form of a core-shell structure where the propolis is the shell and the *Eucalyptus* oil is in the core, wherein the propolis nanoparticles have a size ranging from 250 to 1000 nm, wherein the one or more substances of secondary effect is one or more selected from the group consisting of an adjuvant, a pharmaceutical, an agrochemical, and a cosmetic, and wherein the one or more substances of interest is one or more selected from the group consisting of an antioxidant, an anticorrosive agent, a photoprotector, a catalyst, a lubricant, a dye, a tetracycline, and an azithromycin.

15. A propolis nanoparticle composition consisting of propolis nanoparticles, organic solvent, water, a *Eucalyptus* essential oil, optionally one or more stabilizers and/or emulsifiers, optionally one or more substances of interest, and optionally one or more substances of secondary effect, wherein the *Eucalyptus* essential oil is encapsulated in the propolis nanoparticles in the form of a core-shell structure where the propolis is the shell and the *Eucalyptus* oil is in the core, wherein the propolis nanoparticles have a size ranging from 250 to 1000 nm, wherein the one or more substances of secondary effect is one or more selected from the group consisting of an adjuvant, a pharmaceutical, an agrochemical, and a cosmetic, and wherein the one or more substances of interest is one or more selected from the group consisting of an antioxidant, an anticorrosive agent, a photoprotector, a catalyst, a lubricant, a dye, a tetracycline, and an azithromycin.

16. The propolis nanoparticle composition according to claim 14, characterized in that said one or more stabilizers and/or emulsifiers are selected from the group consisting of alginic acid, polyvinyl alcohols, alginates, agar, carragheen, a cellulose, cetyl dimethicones, copolyols, detergents, dodecyl sodium sulfate, lecithin, sucrose fatty esters, esters of fatty acids with polyglycerol, esters of castor oil acid interesterified with polyglycerol, esters of fatty acids with propyleneglycol, phospholipids, gums, starched pectin, polyethyleneglycol and its copolymers, polyethylenes and their copolymers, polyoxyethylenes and their copolymers, ethylene oxide, a polysorbate, polyvinylpyrrolidone, amphiphilic proteins, mono- and di-glycerides, soaps, glycerol monoestearate, sodium oletate, ammonia phosphate, sucrose acetate isobutyrate, homopolysaccharides, heteropolysaccharides, esteraroyl-2-lactyl sodium lactate, sodium citrate, disodium phosphate, estearylamine, oleylamine, 1-2-dioleoyl-3-trimethyl-ammonium propane, alkylsulfates, 2-dodecoxyethanol, and polyoxyethylene lauryl ether.

17. The propolis nanoparticle composition according to claim 14, characterized in that said stabilizer and/or emulsifier consists of polyvinyl alcohol, phospholipids and/or polysorbates.

18. The propolis nanoparticle composition according to claim 14, characterized in that the one or more substances of interest consist of a tetracycline or a azithromycin.

19. The propolis nanoparticle composition according to claim 14, characterized in that the substances of secondary effect consist of adjuvants.

20. The propolis nanoparticle composition according to claim 14, characterized in that said one or more substances of secondary effect is one or more selected from the group consisting of a pharmaceutical, an agrochemical, and a cosmetic.

21. The propolis nanoparticle composition according to claim 14, characterized in that said organic solvent consists of one or more selected from the group consisting of: ethanol, isopropanol, n-butanol, sec-butyl alcohol, tert-butyl alcohol, ethyl ether, diethyl ether petroleum ether, methyl ether, dimethyl ether, benzyl alcohol, propyleneglycol, polypropyleneglycol, dimethylsulfoxide, ethyleneglycol, n-propyl alcohol, methyl alcohol, acetone, propanone, butanone, butanodione, dichloromethane, trichloromethane, polyethyleneglycol, glacial acetic acid, carbon tetrachloride, perchlorethylene, methylene chloride, n-hexane, styrene, xylene, toluene, benzene, ethyl acetate, 1,4-dioxane, tetrahydrofurane (THF), acetonitrile, dimethylformamide, n-butanol, n-propanol, formic acid, and cyclohexane.

22. The propolis nanoparticle composition according to claim 14, characterized in that said organic solvent is one or more selected from the group consisting of: ethanol, acetone, dichloromethane, trichloromethane and hexane.

23. The propolis nanoparticle composition according to claim 14, characterized in that the *Eucalyptus* essential oil is at least one selected from the group consisting of *Eucalyptus globulus* essential oil, *Eucalyptus citriodora* essential oil, and *Eucalyptus straigeriana* essential oil.

24. The propolis nanoparticle composition according to claim 1, characterized in that the propolis nanoparticles have a size ranging from 250 to 1000 nm.

* * * * *